United States Patent [19]
Gallagher et al.

[11] Patent Number: 5,171,309
[45] Date of Patent: Dec. 15, 1992

[54] POLYESTERS AND THEIR USE IN COMPOSTABLE PRODUCTS SUCH AS DISPOSABLE DIAPERS

[75] Inventors: Francis G. Gallagher; Cathy J. Hamilton, both of Wilmington, Del.; Steven M. Hansen, Kinston, N.C.; Hyunkook Shin; Raymond F. Tietz, both of Wilmington, Del.

[73] Assignee: E. I. Du Pont de Nemours and Company, Wilmington, Del.

[21] Appl. No.: 834,792

[22] Filed: Feb. 13, 1992

Related U.S. Application Data

[63] Continuation-in-part of Ser. No. 771,019, Oct. 1, 1991, which is a continuation-in-part of Ser. No. 645,849, Jan. 25, 1991, Pat. No. 5,097,004, Ser. No. 645,995, Jan. 25, 1991, Pat. No. 5,097,005, and Ser. No. 522,134, May 11, 1990, Pat. No. 5,053,482.

[51] Int. Cl.$^5$ .................. A61F 13/46; C08G 63/199; C08G 63/20; C08G 63/672
[52] U.S. Cl. ......................... 604/365; 47/74; 220/DIG. 30; 428/35.5; 428/36.1; 428/36.4; 428/36.92; 428/287; 428/296; 428/480; 428/481; 521/182; 521/905; 528/300; 528/301; 528/302; 528/307; 528/308; 528/308.6
[58] Field of Search ............... 528/300, 301, 302, 307, 528/308, 308.6; 604/365, 372, 378; 521/182, 905; 428/481, 287, 296, 480

[56] References Cited

U.S. PATENT DOCUMENTS

| | | | |
|---|---|---|---|
| 3,018,272 | 1/1962 | Griffing et al. | 528/293 |
| 3,385,831 | 1/1968 | Watson | 260/75 |
| 3,853,820 | 12/1974 | Vaehon | 528/295 |
| 4,418,116 | 11/1983 | Scott | 428/288 |
| 4,483,976 | 11/1984 | Yamamoto et al. | 525/275 |
| 4,526,738 | 7/1985 | Miyoshi et al. | 428/369 |
| 4,883,706 | 11/1989 | Grosjean | 428/215 |
| 5,097,004 | 3/1992 | Gallagher et al. | 528/272 |
| 5,097,005 | 3/1992 | Tietz | 528/272 |

OTHER PUBLICATIONS

Ingomells, *J. Appl. Pol. Sci.,* vol. 26, 4087–4101 (1981).
Grassie, Developments in Polymer Degradation-5 112–119 (1984), Applied Science Publisher.

*Primary Examiner*—James C. Cannon

[57] ABSTRACT

The invention provides novel polyesters, fibers and films, nonwovens from the fibers and disposable products of the polyesters such as diapers. The products are degradable under the conditions typically existing in waste composting processes, have low ingredient costs and yet provide strength and toughness properties adequate for end uses such as in disposable diapers. The polyesters are based upon polyethylene terphthalate copolymerized with a cycloaliphatic diacid, preferably hexahydroterephthalic acid, and containing alkali metal or alkaline earth metal sulfo groups, such as a metal 5-sulfoisophthalic acid derivative.

11 Claims, No Drawings

POLYESTERS AND THEIR USE IN COMPOSTABLE PRODUCTS SUCH AS DISPOSABLE DIAPERS

CROSS-REFERENCE TO RELATED APPLICATIONS

This application is a continuation-in-part of our co-pending application Ser. No. 07/771,019, filed Oct. 1, 1991, is now pending which is itself a continuation-in-part of the copending application filed by Gallagher, Hamilton and Tietz as Ser. No. 07/645,849, now U.S. Pat. No. 5,097,004, and of the copending application filed by Tietz Ser. No. 07/645,995, now U.S. Pat. No. 5,097,005, both filed Jan. 25, 1991, and a continuation-in-part of copending parent application Ser. No. 07/522,134, filed by Tietz, May 11, 1990, now U.S. Pat. No. 5,053,482.

FIELD OF THE INVENTION

This invention relates to novel polyesters and products therefrom. The products include fibers, films, foams, coated papers, extruded nets, molded objects and nonwovens and disposable products such as diapers from such products. The products are degradable to innocuous materials under conditions used in municipal solid waste composting systems.

BACKGROUND OF THE INVENTION

The inadequate treatment of municipal solid waste which is being put in landfills and the increasing addition of nondegradable materials, including plastics, to be municipal solid waste streams are combining to reduce drastically the number of landfills available and to increase the costs of municipal solid waste disposal. While the recycling of reusable components of the waste stream is desirable in many instances, there are some products which do not readily fit into this framework, e.g. disposable personal absorbents such as diapers and sanitary napkins, garbage bars, and numerous other products. The composting of non-recyclable solid waste is a recognized and growing method of reducing solid waste volume for landfilling and/or making a useful product from the waste to improve the fertility of fields and gardens. One of the limitations to marketing such compost is the visible contamination by undegraded plastic such as film and fiber fragments. As related in the aforesaid parent applications, which are hereby specifically incorporated herein by reference, there was a desired to achieve several objectives, as follows:

1- to provide components which are useful in disposable products and which are degraded into less contaminating forms under the conditions typically existing in waste composting processes. These conditions may involve temperatures no higher than 70° C., and averaging more nearly 55°-60° C., humid conditions as high as 100% relative humidity, and exposure times which range from two weeks to more than three months.

2 -to provide disposable components which will not only degrade aerobically/anaerobically in composting, but will continue to degrade in the soil or landfill. As long as water is present, they will continue to break down into low molecular weight fragments which can be ultimately biodegraded by microorganisms completely into biogas, biomass and liquid leachate, as for natural organics like wood.

3 - to provide novel polyesters for making the aforementioned fibers, films, coatings and nonwoven sheets of the polyesters, and disposable diapers containing the nonwoven sheets.

4 - to provide polyester and derivative products which have low ingredient costs and yet provide strength and toughness properties adequate for end uses such as in disposable diapers.

Accordingly, as described therein, useful novel polyesters were provided and fibers, non-woven sheet, films and combinations thereof, and disposable diapers comprising such materials. Such polyesters are useful for some end uses, e.g., as described. It would, however, be desirable to provide additional degradable materials, having properties that may be better adapted for various end uses. In particular, it is desirable to provide additional polyesters having good rates of hydrolysis.

Abbreviations and nomenclature herein, except as otherwise indicated, are as described in aforesaid U.S. Pat. No. 5,053,482, and applications Ser. Nos. 07/645,849 and 07/645,995, which are hereby incorporated herein by reference, as are applications Ser. Nos. 07/769,414 and 7/769,417 filed by Gallagher et al. Oct. 1, 1991, and applications Ser. Nos. 834,795, 834,796, 834,794, 834,743, 834,791, and 834,797 being filed at the present time.

DESCRIPTION OF RELATED ART

Various polyester compositions have been suggested in the past for biodegradable end uses. These include polyhydroxybutyrate, polylacetide, polycaprolactone, polyglycolide, and their copolymers. They have not been widely adopted in high volume uses, however, because they are either too expensive or their properties are inadequate for the uses mentioned above.

It is known to use salts of 5-sulfoisophthalic acid and its esters as comonomers to improve acid dyeability of polyethylene terephthalate fibers, see for example U.S. Pat. No. 3,018,272 (Griffing et al.). Moreover, this type of fiber is known to have an increased rate of hydrolytic degradation, see for example J. Appl. Poyl. Sci., vol. 26, 4087-4094 (W. Ingamells et al.) and Developments in Polymer Degradation 5, edited by N. Grassie, Applied Science Publishers, 1984, pages 112-119. The use of 5-sulfoisophthalate salts together with neutral comonomers has been disclosed to increase dye rates, but the proportion of the neutral comonomer is usually minimized to affect physical properties as little as possible, see for example U.S. Pat. Nos. 4,704,329 (Hancock et al.) and 3,853,820 (Vachon).

It is also known to use as much as 20 to 45 mole % diethylene glycol as a comonomer with ethylene glycol and terephthalic to provide polyesters having suitable melting and bonding characteristics for a nonwoven binder fiber, see for example U.S. Pat. No. 4,418,116 (Scott). Further, it is known to prepare water dispersible papermaking binder fibers which are made containing 5 to 20 mole % of diethylene glycol and preferably more than 3 mole % 5-sulfoisophthalate, see for example U.S. Pat. No. 4,483,976 (Yamamoto et al.). In the latter patent each of the specific polymers disclosed contain 7 mole % or more of the 5-sulfoisophthalate salt.

SUMMARY OF THE INVENTION

The present invention is based on our finding that polyesters similar to those of the aforesaid copending applications, but including hexahydroterephthalate (HT) radicals in the molecule, instead of part of the para-phenylene (T) units, provide particularly useful shaped articles, such as fibers, that have advantageous properties.

In one embodiment of the invention there is accordingly, provided a novel fiber and film forming polyester consisting essentially of recurring structural units of formula (I)

—C(O)—R—C(O)—OGO— wherein about 10 to 40 mole % of R is a 1,4-cyclohexylene radical, with the remainder being arylene, at least about 85 mole % of which is p-phenylene radical, wherein about 5 to 30 mole % of G is a polyehtylene ether radical selected from the group consisting of —$(CH_2)_2$—O—$(CH_2)_2$— and —$(CH_2)_2$—O—$(CH_2)_2$—O—$(CH_2)_2$—, with the remainder of G being a hydrocarbylene radical selected from the group consisting of —$(CH_2)_2$—, —$(CH_2)_3$—, and —$(CH_2)_4$—O radicals, optically with inclusion of a polyalkylene ether radical of molecular weight at least about 250, and wherein about 0.1 to about 2.5 mole %, of the polymer contains alkali metal or alkaline earth metal sulfo groups, preferably a sodium 5-sulfo-1,3-phenylene radical, especially about 1.5 to about 2 mole % of the groups.

If desired, as indicated, some of the G may be a radical of a polyalkylene glycol of (number average) molecular weight (MW) at least about 250, as disclosed in copending Application Ser. No. 07/645,849, e.g. polyethylene gylcol (PEG).

Other embodiments of the invention include fibers, foams, films and coatings of the above polyesters and nonwovens of the fibers. The invention also contemplates disposable products, such as diapers, which contain an absorbent body portion, with, on at least one surface, a water permeable sheet composed of the polyester, preferably in the form of fibers, a water impermeable sheet of the polyester, or a combination thereof.

It is a finding of the invention that such polyesters, derived from a cycloaliphatic diacid such as hexahydroterephthalic acid (abbreviation HT), as well as from terephthalic acid (abbreviation T), a metal salt of a 5-sulfoisophthalic acid (abbreviation 5SI), ethylene glycol (abbreviation 2G) or other lower alkylene glycol (such as 3G and 4G), and polyethylene ether gylcols (abbreviations DEG or TEG), and, if desired, a $C_2$-$C_4$ polyalkylene ether glycol of the indicated higher molecular weight (such as PEG), undergo degradation when subjected to the conditions of moisture and temperature that typically characterize composing operations. It is also significant that the bulk of the monomers resulting from degradation, i.e. the acids and the glycols, are readily digested by organisms in solid waste or compost to create carbon dioxide, methane and water.

A preferred polyester of the invention is that indicated by the abbreviation 2G/DEG-T/5SI/HT, containing about 7.5 to 21 mole % of DEG, and containing about 1.5 to 2.5 mole % of 5SI and about 14 to 30 mole % of hexahydroterephthalic acid. As in the aforesaid applications, numbers are used to connote the mole percentages of the glycol and of the diacid monomeric units in the polyester, while any PEG content may be denoted in weight (w) % of the total polymer, if so indicated, or by numbers like the other mole percentages if not so indicated.

These polyesters provide useful materials having applications in end uses where containment of body fluids in necessary and disposability is desirable, e.g., in degradable sheet of fabric or film or of paper or fabric coated with a film which will conform easily to body contours yet act as an effective barrier to penetration of body fluids. It is especially preferred that such sheets should have a reduced tendency to rattle and rustle when flexed during body movements. Such a sheet must have adequate strength and toughness to allow its survival during use. In order that it not leave objectionable residues when disposed of, it should disintegrate quickly when placed in proper waste disposal facilities and, ultimately, degrade substantially completely to innocuous materials, such as carbon dioxide, methane and water.

Many copolyesters which are copolymerized with 5-sulfoisophthalic acid (5SI) will hydrolyze readily. Not all such copolymers are acceptable in the end uses contemplated. The polymers should exhibit the desired physical properties, and be processable under practical conditions, but the products of hydrolysis should desirably have the potential to be digested by the organisms likely to be found in waste disposal facilities and compost. This cannot be achieved by all monomers used in preparing other copolyesters. We have found, for example, the terephthalic acid is decomposed substantially completely in such a test over 28 days, and that ethylene glycol and polyethylene glycol (with MW 250 and 3500) are also satisfactorily digested by organisms typical of those found in waste disposal systems; typically, as the molecular weight increases, degradation generally becomes slower. Hexahydroterephthalic acid is also decomposed rapidly. Sodium dimethyl 5-sulfoisophthalate, which has shown slower degradation in these tests, constitutes only a very small proportion of the copolymers, 4-sulfophthalic acid (4SP) has been used in stead of 5SI in related compositions, and has shown complete decomposition in certain tests, so may sometimes be preferred, if this is an important consideration. In this regard, it should be recognized that the rate and extent of decomposition is affected significantly by selection of particular organisms and other specifics during composting.

DETAILED DESCRIPTION OF PREFERRED EMBODIMENTS

The polyesters of the invention consist essentially of recurring structural units of formula I

—C(O)—R—C(O)—OGO— wherein about 10 to 40 mole % of R is a 1,4-cyclohexylene radical, with the remainder being arylene, at least about 85 mole % of which is p-phenylene radical wherein about 5 to 30 % of G is a polyethylene ether radical selected from the group consisting of —$(CH_2)_2$—O—$(CH_2)_2$— and
—$(CH_2)_2$—O—$(CH_2)_2$—O—$(CH_2)_2$—, with the remainder of G being a hydrocarbylene radical selected from the group consisting of —$(CH_2)_2$—, —$(CH_2)_3$—, and —$(CH_2)_2$— radicals, optionally with inclusion of a polyalkylene ether radical of molecular weight at least about 250, and wherein about 0.1 to about 2.5 mole %, of the polymer contains alkali metal or alkaline earth metal sulfo groups, preferably a sodium 5-sulfo-1,3-phenylene radical, especially about 1.5 to about 2 mole % of such groups.

Thus, of the R radicals, about 10 to 40 mole % should be the cycloalkylene residue from hexahydroterephthalic acid, which is a non-aromatic dibasic acid, with at least about 85 mole % of the remainder (about 60 to 95 mole %) being T (para-phenylene), with optional inclusion of up to about 15 mole % of I (meta-phenylene).

Of the G radicals, about 5 to 30 mole %, preferably 7.5 to 21 mole %, are DEG and/or TEG (i.e., polyethylene ether radicals $-(CH_2)_2-O-(CH_2)_2-$ and $-(CH_2)_2-O-(CH_2)_2-O-(CH_2)_2-$, respectively). Optionally, if desired, some may be PEG (a radical of a polyalkylene glycol of MW at least about 250), with the remainder being 2G, 3G and/or 4G (i.e. $C_2-C_4$ lower alkylene groups).

Importantly, the polymer contains sulfo groups, such as are described in U.S. Pat. No. 3,018,272 (Griffing and Remington), the disclosure of which is hereby incorporated by reference. The amount of sulfo groups in the polymer should be about 0.1 to 2.5 mole %. Thus, about 0.1 to 2.5 mole % of the R may be 5SI and/or 4SP radicals, as described herein, or may be another sulfo group suggested by Griffing et al. Or, if desired, about 0.1 to 2.5 mole % of the G may be the sulfo group. Thus the content of sulfo group-containing radical is calculated with respect to the recurring structural units of the formula [—C(O)—R—C(O)—OGO—]. Such radicals may, however, be contained in other units, i.e., other than in the R or G units, for instance in end groups, if desired. The radicals containing sulfo groups need not necessarily be aromatic, although 5SI and 4SP have given good results. Preferred amounts are about 1.5 to 2 mole %. Such components is not only relatively costly but also excessively large amounts can render the polyesters water soluble and thus affect the fiber and film physical properties such as shrinkage. As little as 0.1 mole % of 5SI contributes significantly to the degradability characteristics of the resultant fibers and films. Alternatively, as indicated, other sulfo group-containing units may be included, as taught in U.S. Pat. No. 3,018,272. In such monomeric units, the metal ion is preferably an alkali metal such as sodium potassium or lithium. However, alkaline earth metals such as magnesium are also useful. A 5-sulfoisophthalate that has given very good results is the sodium salt.

The polyesters of the invention are not soluble in water (in contrast to polyesters derivable from ethylene gylcol (2G) and terephthalic acid (T) with higher mole percentages of 5SI). They also have relatively low glass transition temperatures, Tg. Advantageously, the Tg of the polyester fibers or films should be no higher than approximately the temperature at which degradation will take place. Since the temperatures in composting operations are often no higher than about 70° C. it is desired that the Tg of the polyester be no more than about 70° C., preferably about 60° C. or below. Commercial unmodified polyethylene terephthalate (abbreviation 2GT) polyester fibers have a Tg of about 80° C. Even a 2G-T polyester containing 2.5 mole % of 5SI has a Tg value of 76° C. The DEG component is useful and important for lowering the Tg, especially using at least about 7.5 mole % DEG to lower the Tg to less than about 60 C. The glycol component advantageously contains the polyethylene ether radical, such as DEG or TEG, in amount such as to achieve an optimum level of degradability without a major sacrifice to fiber and film physical properties such as tensile strength.

As for the hexahydroterephthalic acid, also, the more of such acid that is added, the more significant is the effect of such incorporation. It is not desirable to lower the melting point of the resulting polymer to such an extent as to impair its usefulness, depending on the desired end-use, and it is generally desirable to incorporate no more than about 40 mole % of such acid. At very high HT contents, the fibers become amorphous, without distinct crystalline melting point. Amorphous fibers are difficult to stabilize and may embrittle over prolonged storage times. Preferred amounts are 10–30 mole %, especially about 14–30 mole %. Apart from compostability, at somewhat lowered melting point (lower than about 220° C.) can be advantageous for providing bondable fibers, especially for bonding together with fibers of 2G-T. At 14% HT, the fiber melting point is lower than about 220° C.

It will be understood that, with minor variations in composition, it is possible for the polyesters of the invention to have a further significant reduction in their Tg values. Such amounts will not otherwise materially alter the degradation characteristics of the polyesters, hence their inclusion is contemplated by the term "consisting essentially" used to described the polyesters and other products of the invention.

Minor amounts of polyfunctional branching agents, such as trimellitic acid residues, may be incorporated to modify melt rheology and film processing, if desired.

A relative viscosity of at least 12, preferably at least about 14, is generally acceptable for melt spinning performance.

The polyesters of the invention may be prepared by conventional polycondensation techniques using, for example, as the glycol component, a combination of about 15 to 20% by weight of the polyalkylene ether glycol, with a complemental molecular amount of ethylene glycol, and, as the acid component, a combination of about 10 to 40 mole % of the hexahydroterephthalic acid, about 55 and 89.9 mole % of terephthalic acid and about 0.1 to 5 mole % of a metal salt of 5-sulfoisophthalic acid, which is a preferred component containing the sulfo groups. DEG is a naturally occurring side product of the polymerisation. Up to approximately 10% by weight of DEG (and/or TEG), corresponding to about 21 mole % DEG, can be generated in the process by adjusting the amount of sodium acetate catalyst and process temperature settings. If necessary, additional DEG may be introduced as a reactant. Optionally up to about 5mole % of the ethylene glycol can be replaced by another glycol. In lieu of the mentioned dicarboxylic acids, ester-forming derivatives such as the dimethyl esters of the acids may be used.

In the Examples herein, the various monomeric components are charged to a polymerization vessel along with an antimony or other catalyst and subjected to polycondensation conditions to produce a linear polyester in which the units are randomly distributed along the molecular chain. It will be understood that it is also possible, however, to first react two or more of the monomeric components to a prepolymer stage, followed by addition of the remaining components, which may be polymeric, and completion of the polymerization.

The polyesters of the invention are very hydrolytically sensitive, having a higher equilibrium moisture content than 2G-T resin and a faster moisture region rate. It is desirable that isolated flake be dried thoroughly, preferably to a moisture content below 400 ppm before reextrusion, and to maintain a nitrogen atmosphere around all possible air in leakage points, and to transfer polymer in warm condition (e.g., above about 50° C.) from the dryer to the extruder.

The polyesters as isolated from the reactor usually have multiple melting points by DSC analysis. These are seen at temperatures which overlap these which might be used in drying 2G-T flake, making it difficult to dry these polymers without fusing the flake into a solid mass when they are rapidly heated to get fast economical drying rates. Slower heating to allow crystallization, after which heating at higher temperatures for fast drying, is desirable.

A desirable procedure for preparing high molecular weight resins from rapidly polymerized lower molecular weight ones may be to use solid phase polymerization of low molecular weight flake. This procedure may desirably be carried out after or in combination with the crystallization procedure mentioned above so that temperatures high enough for rapid polymerization can be attained without fusing of the flaked resin. In addition, as known from U.S. Pat. No. 3,544,523, anticaking agents may be useful to prevent sticking, such as Cab-o-sil grade MS-75D, or other finely divided inert solids, like $TiO_2$, talc, carbon black and clay.

If it is desired, for environmental or other reasons, to avoid use of a catalyst that comprises antimony or another heavy metal, then this may be achieved, for instance, by using a crystalline sodium aluminosilicate molecular sieve such as Linde Molecular Sieve 13X ,type 9356, with a nominal pore size of IOA, obtained from Union Carbide Corporation. Such procedure is more fully described "by Jackson in U.S. Pat. No. 5,041,525, issued Aug. 20, 1991, but other methods of avoiding antimony may be used, if desired.

In any event, the particular mole percentages of the aforementioned components are desirably selected to provide a polyester which in fiber or film form has a Tg of 70° C. or less, preferably of about 60° C. or less.

As will be understood, while the polyesters of the invention are well suited for use as fibers or filaments in nonwoven sheets, they can be used to particular advantage in the form of cast and blown films, foams, coatings, laminates, molded articles, or wherever polyesters with such properties are desired.

Fibers and filaments herein are interchangeable terms in the general sense, but where a more specific acknowledgement of length is appropriate, the term "fibers" is intended to refer to short filaments as in "staple fibers". Hereafter only one of the terms may be used.

The polyesters of the invention may be converted to fibers or filaments by conventional melt spinning techniques. Deniers of 2 to 15 dpf are most common. The filaments may be used as-spun(undrawn) or in a stretched (drawn or oriented) condition. Drawing to reduce denier or for increasing orientation can be accomplished by the usual procedures.

The polymer compositions of the invention can be formed into nonwoven fabrics via a number of processes. These may be roughly divided into spunbounded fabrics and those fabrics using staple fibers. These are discussed in "Encyclopedia of Textiles, Fibers and Nonwoven Fabrics", Ed. Martin Grayson, John Wiley and Sons, New York, 1984, pp. 252-304. The compositions described herein can be used in many such products. Spunbonded nonwovens can be prepared by spinning and laying down simultaneously into webs of continuous filaments using known methods of distributing the threadline in the desired orientation in the web plane. Such webs can be thermally bonded under suitable conditions of time, temperature and pressure to strong fabrics with tensile properties which are usually superior to those obtained with stable webs. Bonding can also be carried out by using suitable adhesives and both these methods may be used to make point bonded or area bonded fabrics. Needle punching may also be used to give the webs stability and strength. Spunbonded fabrics can also be made by melt blowing wherein a stream of molten polymer is extruded into a high velocity stream of heated air and a bonded web formed directly on a screen conveyor from the resultant fibers. Nonwoven fabrics can also be made by direct extrusion through a rotating die into a netlike product (U.S. Pat. No. 3,959,957 J. J. Smith) or by stretching and drawing embossed films of the thermoplastic polymers (British Patent 914,489 and 1,548,865 to Smith and Nephew Research Ltd.).

Staple fibers can be made into nonwovens by several processes. Most of these can be classified into (I) web preparation and (2) reinforcing ("Manual of Nonwovens", Dr. Radko Krema, Textile Trade Press, Manchester, England, pp 74–76, 1971). During web preparation, bales of staple fiber are opened and formed into a web having either a random orientation (via air, water or electrostatic deposition) or parallel or crosslaid orientation (via carding and plying). Reinforcement to impart physical integrity and useful mechanical properties can be accomplished by mechanical means such as needle punching or hydroentanglement (where water jets move fibers out of the plane of the web and entangle them) as in the spunlaced fabrics (U.S. Pat. No. 3,485,706 to Du Pont) or by stitchbonding where a reinforcing thread is sewn through the web. (See "Principles of stitch Through Technology" Nonwovens Fabrics Forum, Clemson University, Clemson, S.C. 1978 by J. D. Singelyn). Reinforcement can also be accomplished by adhesive bonding which includes impregnation of the web by a water based resin binder solution or dispersion and subsequent evaporation of the water leaving a fabric which is composed typically of 60–70% by weight fiber and 30–40% by weight binder. Dry adhesive powders may be applied to the staple web prior to a heating step to produce a powder-bonded nonwoven. Webs of thermoplastic staple fibers may also be reinforced by thermal bonding in which use is made of the ability of the fibers to soften and adhere to each other upon application of heat. As with the spunbonded fabrics these may be point bonded or area bonded. Heat may be applied by hot air (known as through air bonding) or by a pair of patterned and/or flat heated rollers which form a nip through which the web passes to achieve bonding. This process may be carried out with 100% thermoplastic fibers or with blends of thermoplastic fibers with fibers which do not thermally bond in the 100% form, i.e., cotton and rayon.

In addition, useful articles can also be made by laminating, extrusion melt coating or adhesively combining the above types of nonwoven fabrics with each other, with films or with staple webs in such a way as to confer desired properties on the combined fabric.

In particular, a fabric made by extrusion melt coating a thin, pinhole-free film of the compositions of this invention on a nonwoven, made by the spunbonded process or by thermally bonding staple from fibers of this invention alone or in combination with other compostable fibers such as cotton or rayon, is aesthetically pleasing and non-fluid permeable.

The compostable polyester fibers described herein may be used in all these methods of preparing nonwovens to yield fabrics which when subjected to composting conditions will be substantially degraded. Thus staple webs of the polyester fibers, as well as blends of these fibers with cotton and rayon, a may be bonded by hydro-entanglement, by needle punching, by wet resin bonding and by dry adhesive bonding. (The adhesives used should be chosen to allow the desired degradation under composting conditions.)

Thermally bonded staple webs of the described compostable polyester fibers can be made in the 100% form or webs containing a significant proportion of these fibers together with cotton and/or rayon may be thermally bonded to fabrics having useful mechanical properties.

Continuous or spun yarns prepared from the compositions described herein may be used to stitch bond webs of fibers such as cotton, rayon or blends of these fibers, or wood pulp, with the compostable polyester fibers of this invention resulting in fabrics which will degrade under composting conditions.

Spunbonded fabrics can be made by thermally bonding webs of continuous fibers prepared from the compostable polyester compositions described herein, and by blow spinning, direct extrusion to nets and drawing of embossed films.

The compostable compositions described herein can be melt extruded as films to coat spunlaced nonwoven fabrics which themselves may be composed of compostable fibers alone or in combination with wood pulp, rayon or cotton.

A process for preparing ultramicrocellular and plexifilamentary products is disclosed in U.S. Pat. No. 3,227,784 (Blades et al) and durable plexifilamentary and microcellular products are described in U.S. Pat. Nos. 3,277,664 (Blades et al) and U.S. Pat. No. 3,081,519 (Blades et al).

Extrusion of foamed plastics has also been described, for example in Modern Plastics Encyclopedia Oct 1990 Vol 67 #11 pp 291-2. In foam extrusion, molten polymer is first mixed with a relatively small amount (e.g. 1 to 15 wgt %) of a blowing agent. The blowing agent used does not have to be a true solvent for the polymer. When the mixture is extruded, the blowing agents expand due to depressurization and/or volatilization to form a microcellular structure. Unlike in flash spinning, most of the blowing agents used do not leave but stay inside the foam. Most commonly used blowing agents are: 1). gaseous materials such as nitrogen and carbon dioxide, 2). low boiling organic solvents such as hydrofluorocarbons (e.g. HFC-134a, 152a, 125), hydrochlorofluorocarbons (e..g, HCFC-2,2, 123, 141b, 142b, 124), and hydrocarbons (e.g. isobutane, pentane). In addition to these types of physical blowing agents, chemical blowing agents are also used to make foams. Chemical blowing agents decompose at elevated temperatures or through chemical reaction to generate gases. Nucleating agents which are finely divided powders such as fumed silica are usually added to encourage the formation of small uniform cells.

Nonwoven webs of the compostable compositions made by the melt blowing process may also be used as an adhesive layer between other nonwoven fabrics.

It is apparent that the fiber, film, foam, and sheet products made from compositions described herein have a great number of applications in products which are disposed of or potentially may be disposed of in composting systems. In addition the compositions have utility in objects made by injection molding, injection blow molding, thermal forming of sheets, rotational molding of powder, extrusion, and pultrusion, which desirably can be disposed of and degraded in composting system. The following is a nonexclusive list of such end uses.

Agricultural mulch
Agricultural mats containing seeds
Nutrients
Adhesive tape substrate
Baby pants
Bags
Bag closures
Bed sheets
Bottles
Cartons
Disposable diapers
Dust bags
Fabric softener sheets
Garment bags
Garbage and lawn waste bags
Industrial bags
Labels, tags
Monofilaments
Packaging materials and structures
Pillow cases
Protective clothing
Surgical drapes
Surgical gowns
Surgical sheets
Surgical sponges
Tampon applicators
Temporary enclosures
Temporary siding
Toys
Wipes.

The invention can provide fluid impermeable sheets which are compostable in typical waste disposal facilities. Preferably these sheets should not rattle or rustle objectionably and should have strength and toughness adequate for use in personal absorbent products, such as disposable diapers.

The fibers, films, foams and nonwoven fabrics prepared form the compositions of the present invention are of particular utility in disposable diapers since in that use they have an enhanced capability of being degraded in a composting operation. Typical examples of disposable diaper constructions are given in U.S. Pat. No. 3,860,003 (Buell) and 4,687,477 (Suzuki et al.), the disclosures of which are incorporated herein by reference. Items which can be made of the compostable compositions of this invention include:

(1) the backsheet film, i.e., the water-impermeable outside layer, which may be a film which is 100% of the compostable composition or it may be a laminated sheet with an nonwoven or web of compostable fibers including cotton or rayon adhered to the film, or it may be a film adhered to a suitable grade of paper, (2) the topsheet, i.e., the water permeable or inner layer, which is a film of a composition of the invention or a nonwoven fabric of the compostable fiber composition or of a blend of the compostable fiber of this invention with cotton or rayon fiber, having a porosity suitable for passing urine quickly to the fluid absorbing pad between the topsheet and backsheet, (3) the fastening tapes which may optionally be made from films or nonwovens of the compositions of the invention; the fastening tapes are typically coated with a pressure sensitive adhesive, (4) the frontal landing strip, which may be made from films of this invention; the frontal landing strip is typically printed with a decorative design and coated with a pressure sensitive adhesive, (5) the flexible foam optionally inserted into the diaper under modest extension to gather the waist, leg openings, and/or barrier leg cuffs may be made from polymers of this invention, (6) hot melt adhesives used to bond the diaper components to one another may be formulated to incorporate polymers of this invention, (7) the leakage shield used at the diaper waist, in front and back, may be made from films of this invention, and may be glued, thermally bonded, or sonically bonded to the topsheet or the topsheet and backsheet, (8) additives to the absorbent cellulose pulp core, which may be short fibers, fibrids, synthetic pulp prepared by flash spinning, or some other mechanically dispersable and finely divided form made from polymers or fibers of this invention, and which serve to increase wet strength of the core, particularly when superabsorbent polymers have been incorporated and pulp content subsequently reduced, (9) other minor components of the diaper which require the combination of compostability and thermoplastic fabrication and/or processing, and

(10) diaper packaging, which may comprise a bag made of film of compositions of this invention, or paper or cardboard coated with film and/or reinforced with fibers of compositions of this invention.

It will be apparent that the products of the invention may contain additives such as dyes, fillers, pigments, plasticizers, etc. Indeed, use of appropriate fillers or other additives may be helpful, as an acceptable way to enhance disintegratability. Use of starch is particularly helpful, as taught in Application (QP-4850). The incorporation of finely divided particulates has likewise been found helpful, for instance incorporating similar amounts of calcium carbonate in similar compositions. As the incorporation of large amounts of such a filler may increase the tendency of articles to embrittle to an extent that could be undersirable for certain end uses, it may be desirable to take steps such as adding a plasticizer to counter such tendency. Indeed, the addition of materials such as low molecular weight polyethylene adipate (Rucoflex Mn=2000) to particulate blends has been found to provide further advantage in accelerating disintegration of related compositions under composting conditions. Also, in regard to such filled articles, microporous films are taught by Moss in U.S. Pat. No. 4,698,372, and similar techniques may be followed with products of the present invention. Advantageous results have also been obtained by using blends of related compositions with tartarates and citrates, such as dibutyl tartarte and triethyl citrate. The addition of low molecular weight polyethylene adipate (Rucoflex Mn=2000) has also been shown to reduce rattle or rustle of films of related polymers. So incorporation of appropriate additives would be expected to be advantageous for the polymers of the present invention.

TEST METHODS

Polyester glass transition temperatures, Tg, are obtained by using a Du Pont model 2910 Differential Scanning Calorimeter. Samples are heated under a nitrogen atmosphere at a rate of 20° C./min to a temperature 10°-20° C. above the melting point, then the melt is cooled using the rapid air quench capability of the instrument. The Tag is determined from the second cycle scan done at 20° C./min. using the internal software to determine the inflection point of the baseline shift.

Polymer melting point, m.p., is determined on the first heating cycle as described in Tg determination. The temperature at which the highest endothermic peak occurs is reported as the polymer melting point.

Number average molecular weight, Mn, is determined by gel permeation chromatography (gpc) versus a standard polyethylene terephthalate sample with an Mn of 22000 and a weight average molecular weight of 44000. Polymers are dissolved in and the analysis is run HFIP (hexafluoroisopropanol) containing 0.01M sodium trifluoroacetate as the solvent. A Waters model 150C ALC/GPC instrument, or its equivalent, is used with two Zorbax PSM-S biomodal columns (sold by E. I. du Pont de Nemours and Company) (or equivalent) in series at 30° C. A refractive index detector was used and data collected at 100 intervals and analyzed via software provided by the instrument supplier.

Carboxyl end groups are determined by titration of an o-cresol solution of the polymer at 115° C. with KOH in benzyl alcohol to a colorimetric endpoint using bromophenol blue as the indicator. Results are reported in eq./$10^6$ grams of polymer.

Inherent viscosity is defined in "Preparative Methods of Polymer Chemistry", W. R. Sorenson and T. W. Campbell, 1961, p. 35. It is determined at a concentration of 0.5 g/100 ml of the indicated solvent at the indicated temperature, usually HFIP at 30° C.

Tensile Properties of fibers and yarns are coded as T/E/M/To for tenacity, elongation, initial modulus, and toughness and are reported in their conventional units of grams per denier, percent, grams per denier, and grams per denier. These are measured on conditioned (65% RH, 70F) samples (3 inch gauge length) in a commercial testing machine at the rate of extension of 50% per minute (unless otherwise indicated). Toughness (To) is measured as the integrated area under the stress-strain curve. Any counterpart properties of fabrics are similarly coded as T/E/M/To and are reported in units of lb./in./oz./sq.yd, percent, lb./in./oz./sq.yd., and lb./in./oz./sq.yd., respectively. Fabric samples are 1 inch ×8 inches (with 5 inches gauge length), are conditioned prior to testing, and are extended in a commercial testing machine at a rate of 100% per minute. Paper laminates in Examples 6 and 7 are tested as 1 inch wide strips at a 5 inch gauge length at 100% E/min after conditioning at 65% RH 70 F. results are reported as T/Emax/Eult/M/To (Tenacity at maximum load-/Elongation at that load/Ultimate elongation at break-/Initial Modulus/Toughness). The corresponding units are lb/in/oz./$yd^2$/%/% /lb/in/oz/$yd^2$/lb/in/oz/$yd^2$.

Relative viscosity is the ratio of the viscosity of a solution of 0.8 gram of polyester dissolved in 10 ml of hexafluoroisopropanol (HFIP) containing 80 ppm $H_2SO_4$ to the viscosity of $H_2SO_4$-containing HFIP itself, both measured at 25° C. in a capillary viscometer and expressed in the same units.

Crimp index is measured by straightening a crimped tow by application of about 0.1 gpd load. Then 0.5 gm clips 66.6 cm apart are attached to the extended tow. The tow is then cut 11.2 cm beyond each clip to give a sample of 90 extended length. The sample is suspended vertically, hanging freely from one of the clips to allow retraction to crimped length. After about 30 secs. clip to clip distance is measured.

$$\text{Crimp Index} = \frac{(66.6 - Lc)}{66.6} \times 100$$

where Lc is the clip-to-clip distance in the free-hanging state.

Crystallinity index is measured by first obtaining a diffractogram as described by Blades (U.S. Pat. No. 3,869,429, col. 12) with some modifications. The high intensity X-ray source is a Phillips XRG-3100 with a long fine focus copper tube. Diffraction is analyzed with a Phillips single axis goniometer equipped with a thetacompensating slit and a quartz monochromatic set to exclude copper $K_b$ radiation. Diffracted radiation is collected in step scanning mode in 0.025 steps with a 1.5 sec. per step count time. The digital data so collected are analyzed by a computer and smoothed by a running fit to second order polynominal. The computer is programmed to define a straight base line which joins the diffractogram tangentially at about 113 and 343. Crystallinity index is defined as $$\frac{A \times 100}{A - B}$$

where A is the intensity of the 18° 010 peak above this base line and B is the intensity of the 20° minimum above this base line. Crystallinity index has been related to percent crystallinity determined by density (see U.S. Pat. No. 4,704,329, col. 8,9). Weight percent crystallinity=0.676 X Crystallinity index.

The invention will be further illustrated by the following Examples wherein, unless otherwise indicated, parts and percentages are by weight and the polymer compositions are mole %, using the same abbreviations. The fibers were analyzed for chemical species by standard gas chromatography techniques, after appropriate pretreatment, e.g. aminolysis to determine contents of glycol radicals, and glycolysis to determine contents of acid radicals.

EXAMPLE 1

The Example demonstrates the preparation of a compostable, thermal-bondable copolymer of the invention from ingredients which include dimethyl hexahydroterephthalate and sodium dimethyl isophthalate-5-sulfonate.

Using a conventional four-vessel continuous polymerization system for polyester coupled to a spinning machine, polymer is prepared and melt-spun into filaments from dimethyl terephthalate (abbreviation, T), and dimethyl hexahydroterephthalate (abbreviation, HT) sodium dimethyl isophthalate-5-isophthlate (abbreviation, 5SI) in a ratio of 81/17/2 mole % of T/HT/5SI. The glycol component of the fiber of this invention contains ethylene glycol (abbreviation, 2G) and diethylene glycol (abbreviation, DEG) which can be produced by reaction, added as an ingredient or both. In this Example DEG was not added as an ingredient but was present in the product fiber at a glycol ratio of 2G/DEG of 80/20 mole %.

Dimethyl hexahydroterephthalate and sodium dimethyl isophthalate-5-sulfonate are added to a mix tank containing ethylene glycol and catalysts. The catalyst is a mixture of manganese acetate, antimony trioxide, sodium acetate, and tetrapropyltitanate in a mole ratio of 4.6/4.3/1.7/1, respectively. The entire mixture is continuously fed from the mix tank to the first vessel where the ester interchange reaction is carried out and diethylene glycol is formed. The temperatures in this vessel range from approximately 65 degrees C. at the top of the column to approximately 232 degrees C. at the bottom. The vessel is operated at atmospheric pressure with a hold-up time of about 65 minutes. Dimethyl terephthalate in molten form is directly metered into the first vessel. Pure, uncatalyzed glycol is metered into the vessel to adjust the catalyst level to approximately 125 ppm Mn based on the polymer to be formed. The ratio ethylene glycol to dimethyl terepthalate/dimethyl hexahydroterephthalate/sodium dimethyl isophthalate-5-sulfate is approximately 2.0 to 1 by mole.

To the liquid monomer product of the ester interchange vessel is added sufficient phosphoric acid to give approximately 95 ppm phosphorus based upon polymer and a sufficient amount of a slurry of 5% TiO2 in ethylene glycol to give approximately 0.3 percent of the delusterant in the polymer. The mixture is then transferred to the second vessel where the temperature is increased to about 245 degrees C. and the pressure is reduced to about 100 mm Hg as polymerization is initiated for about 26 minutes in the conventional manner. Excess glycol, including ethylene glycol ad diethylene glycol, is removed through a vacuum system.

The low molecular weight material is then pumped to a third vessel where the temperature is increased to about 270 degrees C. and the pressure is reduced to about 45 mm Hg. Excess glycol is again removed through a vacuum system over a period of about 12 minutes.

The low molecular weight material is then transferred to a fourth vessel where the temperature is controlled at approximately 285 degrees C. and the pressure is reduced to 3-10 mm Hg. The pressure is automatically adjusted to maintain the polymer melt viscosity determined by an in-line viscometer. After about 200 minutes, the polymer is recovered and found to have a relative viscosity (RV) of approximately 15. Upon analysis, the polymer composition was determined to be composed of acid-based units having about 81/17/2 mole % of T/HT/5SI and of glycol-based unit shaving about 80/20 mole % 2G/DEG.

The polymer is then spun into amorphous monomcomponent filaments by extruding through orifices (of about 0.38 mm diameter) of a spinneret maintained at 270 degrees C. As the filaments exit the spinneret, they are quenched with air at 21 degrees C, collected into a bundle, and then about 0.29% of a spin finish is applied. The filaments were wound at 1200 yards per minute to give a yarn containing 900 filaments and a total denier of 4500.

Bundles of yarn were collected forming a tow of approximately 36,000 filaments which were drawn in a single stage at a draw ratio of about 3.2×. The fibers were crimped in a stuffer box crimper and heat-set under essentially no restraint in an oven for 8 minutes at 110 degrees C. The resultant filaments have a denier of 2.7, a tenacity of 1.7 grams/denier, a shrinkage in boiling water of 5.4%, a crimp level of 13-14 crimps per inch and a crimp index of approximately 20.

EXAMPLE 2

This was similar to Example 1 except that, after drawing to a draw ratio of 3.2×, the fibers were heat-treated at constant length (under tension) using electrically heated rolls set at 150 degrees C. Fibers were then crimped in a stuffer box crimper and dried in an oven at 90 degrees C. for 8 minutes. The resultant filaments had a denier of 2, a tenacity of 2.3 grams/denier, a shrinkage in boiling water of 9.3%, a shrinkage in dry heat at 150 degrees C. of approximately 32%, a crimp level of 11-12 crimps per inch, and a crimp index of approximately 26.

EXAMPLE 3

Using a conventional four-vessel continuous polymerization system for polyester coupled to a spinning machine, polymer was prepared and melt spun into filaments from dimethyl terephthalate, hydrogenated terephthalate and sodium dimethylisophthalate-5-sulfonate acid components. The glycol component of the fibers of this example contained ethylene glycol and diethylene glycol which was both generated by reaction and added as an ingredient.

Sodium dimethyl isophthalate-5-sulfonate was added to a mix tank containing ethylene glycol and catalysts. The catalyst is a mixture of manganese acetate, antimony trioxide, sodium acetate, and tetrapropyltitanate in a mole ratio of 32.0/15.3/2.1/1.0, respectively. The entire mixture is fed to the first vessel where the ester interchange reaction is carried out. A stream containing diethylene glycol is metered into the catalyzed glycol stream before entering the first vessel. Approximately 50% of the DEG in the polymer was added as an ingredient with the remaining portion being generated by reaction. The temperatures in the first vessel from approximately 65 C at the top of the column to approximately 240 C at the bottom. The vessel is operated under atmospheric pressure with a hold-up time of approximately 60 minutes. Pure, molten dimethyl terephthalate and hydrogenated terephthalate are metered directly into the first vessel in separate streams. The ratio of dimethyl terephthalate to hydrogenated terephthalate is adjusted to give approximately a 4 to 1 ratio, the catalyzed glycol stream is adjusted to give approximately 2 mole % 5SI in the polymer formed and a Mn level of about 260 ppm in polymer. The ratio of 2G to the T/HT stream is approximately 2 to 1 by mole.

Sufficient phosphoric acid is added to the liquid monomer product to give approximately 60 ppm phosphorus based on polymer. A 5 wt % $TiO_2$ slurry in ethylene glycol is added to the monomer to give approximately 0.3 wt % of the delustrant in polymer. The mixture is then transferred to the second vessel where the temperature is increased to about 246 C and the pressure is reduced to approximately 110 mm Hg with a hold-up time of approximately 30 minutes. Excess glycol including ethylene glycol and diethylene glycol is removed through a vacuum system and polymerization is initiated.

The low molecular weight material is then pumped to a third vessel where the temperature is increased to about 275 C and the pressure is reduced to approximately 35 mm H. Glycol is again removed through a vacuum system over a period of about 30 minutes.

The prepolymer is then transferred to the fourth vessel where the temperature is controlled at approximately 288 C and the pressure is reduced to about 3 mm Hg. The pressure is automatically controlled to maintain the polymer melt viscosity determined by an in-line viscometer, after about 200 minutes the polymer is recovered and found to have a relative viscosity of approximately 14.5. Upon analysis the polymer composition was determined to be composed of acid based units having about 77/21/2 mole % of T/HT/5SI and of glycol based units having about 92/8 mole % of 2 G/DEG.

The polymer is then spun into amorphous monocomponent filaments by extruding through orifices (of about 0.38 mm diameter) of a spinneret maintained at 270 C. As the filaments exit the spinneret, they are quenched with air at 22C (20 wet bulb temperature), collected into a bundle, and then approximately 0.2% of a spin finish is applied. The filaments are collected at 1500 yards per minute and 16 ends containing 900 filament-per-end are collected to give a total denier of about 72000.

Bundles of filaments were collected into a tow of approximately 196000 filaments and were drawn in a single stage at a draw ratio of about 3.1×. The fibers were crimped in a stuffer box crimper and heat-set under essentially no restraint in an oven for about 12 minutes at 128 C. The resultant filaments have a denier of about 1.8, a tenacity of about 2.8 grams/denier, a dry heat shrinkage (at 140 C) of about 19%, a crimp level of about 12 crimps-per-inch and crimp index of about 23.

EXAMPLE 4

This was similar to Example 3 except that a tow containing 16 ends and approximately 14400 filaments was drawn approximately 3.3× in a single stage. The fibers were crimped in a stuffer box crimper and heat-set under essentially no restraint in an oven for about 8 minutes at 75 C. The resultant filaments have a denier of 1.43 with a tenacity of 2.9 grams/denier and an elongation of about 27%. The fiber had a crimp level of approximately 10 and a crimp index of about 16.

EXAMPLE 5

This was similar to Example 3 except that a tow containing 16 ends and approximately 28800 filaments was collected and crimped in a stuffer box crimper without drawing. The linear speeds of the rolls were adjusted to apply tension to the tow band before crimping. The crimped fibers were dried and heat set in an oven for about 8 minutes at 70 C. The resultant filaments have a denier of 3.6 with a tenacity of about 0.4 grams per denier and an elongation of about 80%. The fibers had a crimp level of about 9 crimps per inch and a crimp index of about 10.

EXAMPLE 6

This was similar to Example 1 except that the ratio of dimethyl hexahydroterephthalate to dimethyl terephthalate was changed so that the ratio became 72/24/2 mole % T/HT/5SI. The polymer was prepared at the same conditions as Example 1 and the recovered polymer was found to have a relative viscosity of about 9. Upon analysis, the fiber composition was determined to be composed of acid-based units having about 72/24/2 mole % of T/HT/5SI and of glycol-based unit shaving about 89/11 mole % 2G/DEG.

The polymer is spun into amorphous monocomponent filaments by extruding through orifices (of about 0.38 mm diameter) of a spinneret maintained at 255 C. The filaments were wound at 1200 yards per minute to give a yarn containing 900 filaments and a total denier of 4500.

Bundles of yarn were collected forming a tow of approximately 36000 filaments which were drawn in a single stage at a draw ratio of about 3.2×. Drawing was done in room temperature water (about 20 C) without heating of the spray draw zone or crimper finish. The fibers were dried in an oven at 50 C for about 8 minutes. The resultant fibers have a denier of 3.4, a tenacity of 0.8 grams per denier, an elongation of about 150%, and a crimp frequency of about 9 crimps per inch.

What is claimed is:

1. A fiber and film forming biodegradable polyester which undergoes hydrolytic degradation when subjected to the conditions of moisture and temperature that typically characterize composting operations to form products readily digested to innocuous materials by organisms typically found in solid waste and compost, said polyester consisting essentially of recurring structural units of the formula:

—C(O)—R—C(O)—OGO— wherein about 10 to 40 mole % of R is a 1,4-cyclohexylene radical, with the remainder being arylene, at least about 85 mole % of which is p-phenylene radical, wherein about 5 to 30 mole % of G is a polyethylene ether radical selected from the group consisting of —(CH$_2$)$_2$—O—(CH$_2$)$_2$— and
    —(CH$_2$)$_2$—O—(CH$_2$)$_2$—O—(CH$_2$)$_2$—, with the remainder of G being a hydrocarbylene radical selected from the group consisting of —(CH$_2$)$_2$—, —(CH$_2$)$_3$—, and —(CH$_2$)$_4$— radicals, optionally with inclusion of a polyalkylene ether radical of molecular weight at least about 250, and wherein about 0.1 to about 2.5 mole % of the polyester is composed of moieties comprising alkali metal or alkaline earth metal sulfo groups.

2. A polyester according to claim 1, wherein about 7.5 to 21 mole % of G is a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$—.

3. A polyester according to claim 1, wherein about 14 to 30 mole % of R is a 1,4-cyclohexylene radical.

4. A polyester according to claim 1, wherein about 1.5 to 2.5 mole % of R is a sodium 5-sulfo-1,3-phenylene radical.

5. A polyester according to claim 1, wherein about 7.5 to 21 mole % of G is a polyethylene ether radical selected from the group consisting of —(CH$_2$)$_2$—O—(CH$_2$)$_2$— and —(CH$_2$)$_2$—O—(CH$_2$)$_2$—O—(CH$_2$)$_2$—, about 14 to 30 mole % of R is a 1,4-cyclohexylene radical, and about 1.5 to 2.5 mole % of R is a sodium 5-sulfo-1,3-phenylene radical.

6. A fiber of the polyester of any one of claims 1 to 5.

7. A non-woven sheet of the polyester of claim 1.

8. A film of the polyester of claim 1.

9. A foam of the polyester of claim 1.

10. A disposable diaper which includes an absorbent body portion having on one surface thereof a water permeable nonwoven sheet of the polyester of claim 1.

11. A disposable diaper which includes an absorbent body portion having on one surface thereof a water impermeable sheet of the polyester of claim 1.

* * * * *